(12) United States Patent
Wang et al.

(10) Patent No.: US 12,225,923 B2
(45) Date of Patent: Feb. 18, 2025

(54) METHODS OF MANUFACTURING NUTRITIONAL FORMULATIONS

(71) Applicant: Clover Corporation Limited, Victoria (AU)

(72) Inventors: Bo Wang, Parkinson (AU); Glenn Elliott, Casuarina (AU); Mek Chu Ting Cheng, Calamvale (AU); Craig Stewart Patch, Fairy Meadow (AU); Brenda Louise Mossel, Tarragindi (AU)

(73) Assignee: Clover Corporation Limited, Altona (AU)

( * ) Notice: Subject to any disclaimer, the term of this patent is extended or adjusted under 35 U.S.C. 154(b) by 0 days.

(21) Appl. No.: 16/068,592

(22) PCT Filed: Apr. 13, 2017

(86) PCT No.: PCT/AU2017/050339
§ 371 (c)(1),
(2) Date: Jul. 6, 2018

(87) PCT Pub. No.: WO2017/177283
PCT Pub. Date: Oct. 19, 2017

(65) Prior Publication Data
US 2019/0014808 A1    Jan. 17, 2019

(30) Foreign Application Priority Data

Apr. 14, 2016 (AU) .................................. 2016901392

(51) Int. Cl.
A23L 33/00    (2016.01)
A23L 33/115   (2016.01)

(52) U.S. Cl.
CPC ............. *A23L 33/40* (2016.08); *A23L 33/115* (2016.08); *A23V 2002/00* (2013.01);
(Continued)

(58) Field of Classification Search
CPC . A23L 33/115; A23L 33/40; A23V 2200/222; A23V 2002/00;
(Continued)

(56) References Cited

U.S. PATENT DOCUMENTS

| | | |
|---|---|---|
| 3,917,859 A | 11/1975 | Terada et al. |
| 4,366,180 A | 12/1982 | Altrock et al. |

(Continued)

FOREIGN PATENT DOCUMENTS

| | | |
|---|---|---|
| CN | 101511356 A | 8/2009 |
| EP | 0970741 | 1/2000 |

(Continued)

OTHER PUBLICATIONS

"International Application No. PCT/AU2017/050339, International Search Report and Written Opinion mailed Jul. 5, 2017", (Jul. 5, 2017), 13 pgs.

(Continued)

*Primary Examiner* — Latosha Hines
(74) *Attorney, Agent, or Firm* — Schwegman Lundberg & Woessner, P.A.

(57) ABSTRACT

The present invention broadly relates to methods for manufacturing nutritional formulations, and nutritional formulations produced by said methods, comprising a fatty acid in a double emulsion (O/W/O emulsion).

7 Claims, 4 Drawing Sheets

(52) U.S. Cl.
CPC . *A23V 2200/222* (2013.01); *A23V 2250/1862* (2013.01); *A23V 2250/1866* (2013.01); *A23V 2250/1868* (2013.01); *A23V 2250/187* (2013.01); *A23V 2250/1874* (2013.01); *A23V 2300/38* (2013.01)

(58) Field of Classification Search
CPC .... A23V 2250/1862; A23V 2250/1866; A23V 2250/1868; A23V 2250/187; A23V 2250/1874; A23V 2300/38
See application file for complete search history.

(56) References Cited

U.S. PATENT DOCUMENTS

| | | | |
|---|---|---|---|
| 4,513,017 A | | 4/1985 | Moran et al. |
| 5,077,077 A | | 12/1991 | Suzuki et al. |
| 5,332,595 A | | 7/1994 | Gaonkar |
| 5,756,719 A | * | 5/1998 | Chaundy ................. C07H 1/00 536/119 |
| 2006/0165735 A1 | * | 7/2006 | Abril ...................... C09K 23/00 424/195.17 |
| 2010/0063142 A1 | * | 3/2010 | Nishiumi ............. A23K 20/158 514/464 |
| 2013/0202662 A1 | | 8/2013 | Nishiumi et al. |
| 2016/0316806 A1 | * | 11/2016 | Gehin-Delval ........ A61K 8/361 |

FOREIGN PATENT DOCUMENTS

| | | | | |
|---|---|---|---|---|
| JP | 07313055 A | | 12/1995 | |
| WO | WO-1996026647 | | 9/1996 | |
| WO | WO-2008044550 A1 | | 4/2008 | |
| WO | WO-2015086388 | | 6/2015 | |
| WO | WO-2015086388 A1 | * | 6/2015 | ............. A23D 7/005 |
| WO | WO-2015147043 A1 | * | 10/2015 | ............. A23D 7/003 |
| WO | WO-2017177283 | | 10/2017 | |

OTHER PUBLICATIONS

Jahaniaval, Firouz, et al., "Characterization of a Double Emulsion System (oil-in-water-in-oil emulsion) with Low Solid Fats: Microstructure", JAOCS, vol. 80, No. 1 (2003), (2003), 25-31.

O'Dwyer, Sandra P., et al., "Effects of Green Tea Extract and α-Tocopherol on the Lipid Oxidation Rate of Omega-3 Oils, Incorporated into Table Spreads, Prepared using Multiple Emulsion Technology", *Journal of Food Science*, 77(22), (2012), N58-N65.

O'Dwyer, Sandra P., et al., "Formation, rheology and susceptibility to lipid oxidation of multiple emulsions (O/W/O) in table spreads containing omega-3 rich oils", *LWT—Food Science and Technology* 51(2), (May 2013), 484-491.

Voss, G., et al., "Production and characterization of emulsions that contain healthy benefiting vegetable oils for introduction in different foods", Nauchni Trudove—Universitet po Khranitelni Tekhnologii, Plovdiv. 2011, vol. 58, No. 1, (2011), 179-184.

Serdaroglu, Meltem, et al., "Multiple emulsions and their applications in food", Proceedings IC FABE, (May 2013), pp. 257-272.

Van Der Graaf, Schroen, et al., "Preparation of double emulsions by membrane emulsification—a review", Journal of Membrane Science 251.1-2, (2005), pp. 7-15.

Edris, A., et al., "Encapsulation of orange oil in a spray dried double emulsion", Nahrung/Food 45 (2001) No. 2, (2001), 133-137.

* cited by examiner

METHODS OF MANUFACTURING NUTRITIONAL FORMULATIONS

PRIORITY CLAIM TO RELATED APPLICATIONS

This application is a U.S. national stage filing under 35 U.S.C. § 371 from International Application No. PCT/AU2017/050339, filed on 13 Apr. 2017, and published as WO2017/177283 on 19 Oct. 2017, which claims the benefit under 35 U.S.C. 119 to Australia Application No. 2016901392, filed on 14 Apr. 2016, the benefit of priority of each of which is claimed herein, and which applications and publication are hereby incorporated herein by reference in their entirety.

TECHNICAL FIELD

The present invention broadly relates to methods for manufacturing nutritional formulations, and nutritional formulations produced by said methods.

BACKGROUND OF THE INVENTION

It is well established that polyunsaturated fatty acids (PUFAs), such as long-chain polyunsaturated fatty acids (LCPUFAs), play a critical role in infant and childhood development. Docosahexaenoic acid (DHA) and arachidonic acid (AA) are considered to be building blocks for a healthy brain, visual acuity and a fully functional nervous system. A large body of research has demonstrated that DHA and AA, which are both present in human milk, are physiologically important in pre-natal and post-natal life during the period of rapid brain and eye development. DHA and AA have been shown to rapidly accumulate in the brain during the last trimester of pregnancy and during the first two post-natal years.

Because of their critical role, especially in infant development, DHA and AA have been incorporated into infant formula for many years as well as being incorporated into other nutritional formula. LCPUFAs, such as DHA and AA, are typically incorporated into nutritional formula, such as infant formula, during manufacture normally by dry blending or direct injection, together with other formula components. Because PUFAs are susceptible to oxidative degradation and tainting, dry blending is generally considered to provide a superior final product. In such dry blending methods, the PUFAs are provided in a powdered microencapsulated form.

Direct injection is more efficient than dry blending. Direct injection involves incorporating neat fatty acids into nutritional formula by direct injection into an oil stream comprising other formula components. Following direct injection, the oil stream is mixed with an aqueous phase, homogenised and spray dried. Generally, the quality of the end infant formula product obtained when using the direct injection method is considered to be inferior when compared to the end product obtained by the dry blending method, particularly in relation to taste and PUFA stability. In this regard, it has been noted that the parameters used during direct injection, such as exposing the PUFAs to high temperatures, oxygen and oxidising agents, facilitate oxidation of PUFAs, result in an inferior product.

SUMMARY OF THE INVENTION

The invention is predicated on the surprising discovery that the quality of nutritional formula and in particular infant formula prepared by direct injection of fatty acids, such as PUFAs, LCPUFAs, medium-chain fatty acids (MCFAs), branched-chain fatty acids (BCFAs) or mixtures thereof, into an oil stream can be improved (in terms of flavour and taste) by incorporation of the fatty acids in a double emulsion.

In particular, it has been found that the double emulsion based methods described herein are able to better stabilise the fatty acids and, in particular, prevent or minimise oxidation of fatty acids during processing involving, for instance, high temperatures.

In one aspect, the present invention provides a method for producing a nutritional formulation comprising one or more fatty acids, said method comprising:
(i) providing a double emulsion of said one or more fatty acids within an edible oil stream such as a vegetable oil by:
 (a) preparing a double emulsion (O/W/O emulsion) characterised by an internal oil phase comprising one or more fatty acids dispersed in an aqueous phase which is in turn dispersed in an external oil phase and dispersing said double emulsion into an edible oil stream such as a vegetable oil; or
 (b) preparing an oil-in-water emulsion (O/W emulsion) characterised by an internal oil phase comprising one or more fatty acids dispersed in an aqueous phase and dispersing said oil-in-water emulsion in an edible oil stream such as a vegetable oil thereby forming said double emulsion in-situ;
(ii) mixing the double emulsion of said one or more fatty acids in the edible oil stream such as a vegetable oil with an aqueous phase; or
(iii) mixing the double emulsion of said one or more fatty acids with an aqueous phase; and
(iv) homogenising the double emulsion mixture of step (ii) or (iii) to form the nutritional formulation.

In a further aspect, the present invention provides a method for producing a nutritional formulation comprising one or more fatty acids, said method comprising:
(i) providing a double emulsion of said one or more fatty acids within an edible oil stream such as a vegetable oil by preparing a double emulsion (O/W/O emulsion) characterised by an internal oil phase comprising one or more fatty acids dispersed in an aqueous phase which is in turn dispersed in an external oil phase and dispersing said double emulsion into an edible oil stream such as a vegetable oil;
(ii) mixing the double emulsion of said one or more fatty acids within the edible oil stream such as the vegetable oil with an aqueous phase; or
(iii) mixing the double emulsion of said one or more fatty acids with an aqueous phase; and
(iv) homogenising the double emulsion mixture of step (ii) or (iii) to form the nutritional formulation.

In a further aspect, the present invention provides a method for producing a nutritional formulation comprising one or more fatty acids, said method comprising:
(i) providing a double emulsion of said one or more fatty acids within an edible oil stream such as a vegetable oil by preparing an oil-in-water emulsion (O/W emulsion) characterised by an internal oil phase comprising one or more fatty acids dispersed in an aqueous phase and dispersing said oil-in-water emulsion in an edible oil stream such as a vegetable oil thereby forming said double emulsion in-situ;

(ii) mixing the double emulsion of said one or more fatty acids within the vegetable oil stream with an aqueous phase; or (iii) mixing the double emulsion of said one or more fatty acids with an aqueous phase; and (iv) homogenising the double emulsion mixture of step (ii) or (iii) to form the nutritional formulation.

In a further aspect, the present invention provides a method for producing a nutritional formulation comprising one or more fatty acids, said method comprising:

(i) providing a double emulsion of said one or more fatty acids within a vegetable oil stream by:

(a) preparing a double emulsion (O/W/O emulsion) characterised by an internal oil phase comprising one or more fatty acids dispersed in an aqueous phase which is in turn dispersed in an external oil phase and dispersing said double emulsion into a vegetable oil stream; or (b) preparing an oil-in-water emulsion (O/W emulsion) characterised by an internal oil phase comprising one or more fatty acids dispersed in an aqueous phase and dispersing said oil-in-water emulsion in a vegetable oil stream thereby forming said double emulsion in-situ;

(ii) mixing the double emulsion of said one or more fatty acids within the vegetable oil stream with an aqueous phase; and (iii) homogenising the double emulsion mixture of step (ii) to form the nutritional formulation.

In a further aspect, the present invention provides a method for producing a nutritional formulation comprising one or more fatty acids, said method comprising:

(i) providing a double emulsion of said one or more fatty acids within a vegetable oil stream by preparing a double emulsion (O/W/O emulsion) characterised by an internal oil phase comprising one or more fatty acids dispersed in an aqueous phase which is in turn dispersed in an external oil phase and dispersing said double emulsion into a vegetable oil stream;

(ii) mixing the double emulsion of said one or more fatty acids within the vegetable oil stream with an aqueous phase; and (iii) homogenising the double emulsion mixture of step (ii) to form the nutritional formulation.

In a further aspect, the present invention provides a method for producing a nutritional formulation comprising one or more fatty acids, said method comprising:

(i) providing a double emulsion of said one or more fatty acids within a vegetable oil stream by preparing an oil-in-water emulsion (O/W emulsion) characterised by an internal oil phase comprising one or more fatty acids dispersed in an aqueous phase and dispersing said oil-in-water emulsion in a vegetable oil stream thereby forming said double emulsion in-situ;

(ii) mixing the double emulsion of said one or more fatty acids within the vegetable oil stream with an aqueous phase; and (iii) homogenising the double emulsion mixture of step (ii) to form the nutritional formulation.

In an embodiment, the method according to one of the above aspects further comprises spray drying the homogenised double emulsion mixture of step (iv).

In particular embodiments of the above aspects the fatty acids are PUFAs, MCFAs, BCFAs, or mixtures thereof. In particular embodiments, the PUFAs are LCPUFAs. The LCPUFAs may be selected from DHA, AA, eicosapentaenoic acid (EPA), docosapentaenoic acid (DPA), α-linolenic acid (ALA), stearidonic acid (SDA), linoleic acid (LA), gamma-linolenic acid (GLA), conjugated linolenic acid (CLA) or mixtures thereof.

The one or more fatty acids may be present as a component of a microbial oil, a plant oil or a fish oil. The fish oil may be, for example, tuna oil.

A further aspect of the invention provides a nutritional formulation when produced by a method of the invention.

In an embodiment, the nutritional formulation is for use as a nutritional supplement. For example, the formulation may be for us as an infant formula or in an infant formula.

Definitions

The following are some definitions that may be helpful in understanding the description of the present invention. These are intended as general definitions and should in no way limit the scope of the present invention to those terms alone, but are put forth for a better understanding of the following description.

Throughout this specification and the claims which follow, unless the context requires otherwise, the word "comprise", and variations such as "comprised", "comprises" or "comprising", will be understood to imply the inclusion of a stated integer or step or group of integers or steps but not the exclusion of any other integer or step or group of integers or steps.

In the context of this specification, the term "about" is understood to refer to a range of numbers that a person of skill in the art would consider equivalent to the recited value in the context of achieving the same function or result.

In the context of this specification, the term "infant formula" includes compositions that are intended as breast milk replacements or supplements and also milk fortifiers.

In the context of this specification, the term "edible" means a non-toxic substance which is considered safe for consumption by humans.

In the context of this specification, the term "long chain" is understood to refer to a saturated or unsaturated hydrocarbon chain having 13 carbon atoms or more.

In the context of this specification, the term "medium chain" is understood to refer to a saturated or unsaturated hydrocarbon chain having 6-12 carbon atoms.

In the context of this specification, the terms "unsaturated" and "polyunsaturated" are understood to refer to fatty acids having one or more double bonds within the fatty acid chain.

In the context of this specification, the term "low molecular weight emulsifier" is understood to mean an emulsifying agent having a molecular weight of 1000 g/mol or less.

In the context of this specification, the term "high molecular weight emulsifier" is understood to mean an emulsifying agent having a molecular weight of greater than 1000 g/mol.

During emulsification, the emulsifier may form a layer at the oil-water interface. A low molecular weight emulsifier may form a monolayer at the interface and may substantially cover the interface. A high molecular weight emulsifier may form a monolayer or a multilayer at the interface. The thickness of a layer formed at the interface may depend on the molecular weight of the emulsifier used. A low molecular weight emulsifier may provide a layer with thickness of about 0.5 to 1.0 nm. A high molecular weight emulsifier may provide a layer with a thickness of about 1.0 to 15 nm.

In the context of this specification, the hydrophile-lipophile balance (HLB) number is used as a measure of the ratio of hydrophilic and lipophilic groups on a surfactant. Surfactants having HLB numbers >10 have an affinity for water (hydrophilic) and surfactants having an HLB number <10 have an affinity for oil (lipophilic). In the context of the present specification, the terms "surfactant" and "emulsifier" are used interchangeably. In certain embodiments of the present invention, reference to "low HLB"-value emulsifiers refers to emulsifiers or surfactants having HLB values less than 10. Additionally, in certain other embodiments, reference to "high HLB"-value emulsifiers refers to emulsifiers or surfactants having HLB values greater than 10.

Emulsifiers with an HLB number >10 may be used to stabilise oil-in-water emulsions and may have a high molecular weight or a low molecular weight. Examples of a high HLB value emulsifier having a high molecular weight may be a casein, globulin in whey proteins, or a polysaccharide such as gum arabic. Examples of a low HLB emulsifier having a low molecular weight include a Span, some lecithins, a free fatty acid, a mono- or diglyceride, a sucrose ester and acetic acid esters of a mono- or diacylglycerol. Emulsifiers with an HLB number <10 may be used to stabilise water-in-oil emulsions and may have a high or low molecular weight. Examples of a low HLB value emulsifier having a low molecular weight include a Span, some lecithins and polyglycerol polyricinoleate.

In the context of this specification, it is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In the context of this specification, "(s)" following a noun means the plural and/or singular forms of the noun.

In the context of this specification, the term "and/or" means "and" or "or" or both.

Although the present invention is broadly as defined above, those persons skilled in the art will appreciate that the invention is not limited thereto and that the invention also includes embodiments of which the following description gives examples.

The embodiments of the invention described herein are intended to be merely exemplary, and those skilled in the art will recognise, or will be able to ascertain using no more than routine experimentation, numerous equivalents of specific materials, compounds, and procedures. All such equivalents are considered to be within the scope of the invention as set out in the accompanying claims.

BRIEF DESCRIPTION OF FIGURES

Embodiments of the invention are described herein with reference, by way of example only, to the following drawings.

DETAILED DESCRIPTION OF THE INVENTION

Embodiments of the present invention provide methods for the preparation of nutritional formulations comprising double emulsions containing one or more fatty acids, in particular PUFAs, LCPUFAs, MCFAs, BCFAs or mixtures thereof. The double emulsions described herein are characterised by an internal oil phase comprising one or fatty acids dispersed in an aqueous phase that is dispersed in an external oil phase. The double emulsions may therefore also be referred to as oil-in-water-in-oil (O/W/O) emulsions.

Without wishing to be bound by theory, the inventors believe that, in accordance with embodiments of the present invention, double emulsions as described herein (characterised by an internal oil phase comprising one or more fatty acids) are able to be efficiently homogenised such that the fatty acids contained therein are not exposed to conditions which accelerate decomposition, such as high processing temperatures and being exposed to oxygen and oxidising agents, during the homogenisation process and the remainder of the nutritional formulation preparation process. Stability of the fatty acids can thereby be enhanced. Improvements in taste likely arise due to minimisation of fatty acid degradation and oxidation products in the formulation. Specifically, the present inventors have now recognised that during processing the formed O/W/O emulsion advantageously protects the fatty acids while being exposed to the high processing temperatures, oxygen, and oxidising agents typically used during direct injection. This provides a formulation with minimal fatty acid degradation, and that has organoleptic properties comparable to formulas comprising fatty acids added as microencapsulated powders through dry blending.

In a first process step, methods according to embodiments of the invention contemplate providing a double emulsion characterised by an internal oil phase comprising one or more fatty acids dispersed in an aqueous phase that is in turn dispersed in an external oil phase.

The one or more fatty acids may be selected from PUFAs, LCPUFAs, MCFAs, BCFAs, or mixtures thereof. The one or more fatty acids may be present as a component of a microbial oil, a plant oil or a fish oil.

In particular embodiments, the fatty acids are PUFAs, such as omega-3 fatty acids, omega-6 fatty acids or mixtures thereof. In further particular embodiments, the PUFAs are LCPUFAs, for example selected from DHA, AA, eicosapentaenoic acid (EPA), docosapentaenoic acid (DPA), α-linolenic acid (ALA), stearidonic acid (SDA) or mixtures thereof.

The one or more LCPUFAs may be present as a component of a microbial oil, a plant oil or a fish oil, for example tuna oil. In one embodiment, the LCPUFA is AA or DHA. In an alternate embodiment, the LCPUFAs are a mixture of DHA and AA.

In other embodiments, the fatty acids may be MCFAs or BCFAs. Exemplary MCFAs include, for example, hexanoic acid (caproic acid), caprylic, capric or lauric acids, or mixtures thereof.

For simplicity, the disclosure herein below makes reference to PUFAs as exemplary fatty acids. However those skilled in the art will appreciate that the scope of the present invention is not limited to this single exemplification.

In one embodiment, the process step to form the O/W/O emulsion involves separately mixing together:
a) an oil-in-water phase comprising an edible oil with water in the presence of at least one emulsifier (oil phase A-external); with
b) an oil-in-water phase comprising at least one or more PUFAs with water in the presence of at least one emulsifier (oil phase B-internal);

for a time and under conditions sufficient to form a double emulsion comprising an internal oil phase which comprises one or more PUFAs dispersed in an aqueous phase (oil phase B) which is in turn dispersed in an external oil phase (oil phase A).

Suitable times and conditions for forming a double emulsion according to the invention would be known to a skilled person, or could easily be determined by the skilled person through routine experimentation.

In another embodiment, the O/W/O emulsion is formed in-situ within the edible oil stream such as a vegetable oil by preparing an oil-in-water emulsion (O/W emulsion) characterised by an internal oil phase comprising one or more PUFAs dispersed in an aqueous phase and dispersing said O/W emulsion in an edible oil stream such as a vegetable oil thereby forming said double emulsion.

The O/W emulsions described herein may comprise one or more emulsifiers. The emulsifier(s) act to stabilise the O/W emulsion. For example, in one embodiment, whereby the O/W/O emulsion is formed in-situ within the edible oil stream such as a vegetable oil, the O/W emulsion comprises one or more emulsifiers to facilitate the formation of the O/W/O emulsion in-situ. The emulsifiers may be high molecular weight emulsifiers, low molecular weight emulsifiers, or a mixture thereof. Emulsifiers suitable for use include any and all edible or food grade emulsifiers. Non-limiting examples include: low molecular weight emulsifiers with a high HLB value, such as Tween emulsifiers, some lecithins, mono- and diacylglycerols; high molecular weight emulsifiers with a high HLB value, such as caseinate, whey protein, polysaccharides with emulsifying groups; and low molecular weight emulsifiers with a low HLB value such as Span emulsifiers, polyglycerol polyricinoleate and some lecithins. In embodiments of the invention, the O/W emulsion comprises a high molecular weight emulsifier and a low molecular weight emulsifier. In one embodiment, the O/W emulsion comprises caseinate and lecithin.

The emulsifiers for oil phase A and B above may be the same or different, and may comprise mixtures of emulsifiers. The emulsifiers may have various HLB ("hydrophile-lipophile balance") values. Accordingly, the use of more than one emulsifier with a range of HLB values may, in some embodiments, provide the advantage of more effective emulsification.

The O/W/O emulsion of the present invention may be prepared by phase inversion. In an embodiment, a first step in the preparation of an O/W/O emulsion by phase inversion comprises the preparation of a first oil phase. In an embodiment, a second step in the preparation of the O/W/O emulsion by phase inversion comprises the preparation of a second oil phase, as distinct from the first oil phase. In an embodiment, the first oil phase may comprise a fatty acid. In an embodiment, preparation of a first or a second oil phase comprises the first step of adding a high HLB-value emulsifier to a water phase. In an embodiment, a high HLB value emulsifier has an HLB value greater than 10. In an embodiment, preparation of a first or second oil phase comprises the second step of adding a low HLB-value emulsifier to an of phase. In an embodiment, a low HLB-value emulsifier has an HLB value lower than 10. In an embodiment, preparation of a first or second oil phase comprises a third step of combining a water phase-high HLB-value emulsifier mixture with an oil phase-low HLB-value emulsifier mixture. In an embodiment, a third step in the preparation of an O/W/O emulsion by phase inversion comprises the combination of a first oil phase and a second oil phase, according to an aforementioned embodiment.

The O/W/O emulsion of the present invention may be prepared by multiple homogenisation. In an embodiment, a first step in the preparation of an O/W/O emulsion of the present invention by multiple homogenisation comprises the first step of preparing an oil-in-water emulsion. In an embodiment, preparing an oil-in-water emulsion comprises the homogenisation of an aqueous phase and an oil phase. In an embodiment, an aqueous phase of a first step of preparing an oil-in-water emulsion comprises adding a high HLB-value emulsifier to a water phase. In an embodiment, a high HLB-value emulsifier has a HLB-value greater than 10. In an embodiment, an oil phase of a first step comprises a low HLB-value emulsifier and an internal oil. In an embodiment, the internal oil is a single oil. In another embodiment, the internal oil is a mixture of oils. In an embodiment, an internal oil of the O/W/O emulsion is a fatty acid. In an embodiment, an internal oil of the O/W/O emulsion comprises at least one fatty acid In an embodiment, a low HLB-value emulsifier has a HLB-value lower than 10.

In an embodiment, a second step in the preparation of an O/W/O emulsion of the present invention by multiple homogenisation comprises the second step of preparing the O/W/O emulsion from an oil-in-water emulsion. In an embodiment, preparing the O/W/O emulsion comprises homogenisation of an oil-in-water emulsion with an external oil phase. In an embodiment, preparing the O/W/O emulsion by homogenisation of an oil-in-water emulsion comprises a first step of preparing an external oil phase. In an embodiment, an external oil phase comprises an external oil and a low HLB-value emulsifier. In an embodiment, the external oil is a single oil. In another embodiment, the external oil is a mixture of oils. In an embodiment, preparing the O/W/O emulsion by homogenisation of an oil-in-water emulsion comprises a second step of blending an oil-in-water emulsion with an external oil phase. In an embodiment, the O/W/O emulsion is prepared by homogenisation of an oil-in-water emulsion with an external oil phase.

In an embodiment, the one or more of the emulsifiers may have a high HLB value. In an embodiment, a high HLB value is an HLB value greater than about 10. In an embodiment, one or more of the emulsifiers may have a low HLB value. In an embodiment, a low HLB value is an HLB value lower than about 10. One or more of the emulsifiers may be a phospholipid-based emulsifier. In an embodiment, an emulsifier used in the preparation of an O/W/O emulsion is a phospholipid-based emulsifier with a medium phosphatidylcholine (PC) content. In another embodiment, an emulsifier used in the preparation of an O/W/O emulsion is a phospholipid with a high phosphatidylcholine (PC) content. In an embodiment, a phospholipid with a high phosphatidylcholine (PC) content has a phosphatidylcholine (PC) content of over 20%. In another embodiment, a phospholipid with a medium phospatidylcholine (OC) content has a phosphatyidylcholine (PC) content of less than 20%. In another embodiment, an emulsifier used in the preparation of an O/W/O emulsion is a phospholipid with a phosphatidylcholine content of over 20%.

The emulsifier(s) may be present in an amount between about 0.01% and 5%, or between about 0.1% and 5%, or between about 0.1% and 5%, of the total mass of the double emulsion. In other embodiments, the emulsifier(s) may be present in an amount between about 0.01% and 5%, or between about 0.1% and 5%, or between about 0.1% and 5%, of the total mass of the O/W emulsion.

The O/W emulsion may comprise between about 30% and about 90% oil, and between about 10% and about 70% water, based on the total mass of the O/W emulsion.

The external oil phase may be present in an amount between about 35% and about 85%, based on the total mass of the double emulsion, for example about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, or about 84%.

The internal oil phase may be present in an amount of between about 10% and about 65%, based on the total amount of the double emulsion, for example about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, or about 64%.

In an embodiment, the amount of total PUFAs in the internal oil phase is about 30 and 90%, based on the total mass of the O/W emulsion in the internal phase, for example about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, or about 89%. In an embodiment, the amount of total PUFAs in the internal oil phase is greater than 65%, greater than 70%, greater than 75%, greater than 80%, or greater than 90%, based on the total mass of the O/W emulsion for the internal phase. In an embodiment, the amount of total PUFAs in the internal oil phase is between about 80% to about 90%, for example about 80% to about 85%, of the total amount of the double emulsion for the internal phase.

The internal oil phase may comprise any edible oil. In some embodiments, the internal oil phase comprises, consists or consists essentially of, oil which is a source of one or more PUFAs, optionally a fish oil, microbial oil, plant oil or their concentrated form. In an exemplary embodiment, fish oil or its concentrated form for use in the present invention may be obtained from, for example one or more of the following fish: tuna, salmon, trout, sea bass, menhaden, pilchards, mackerel, sardines, herring, kipper, eel, whitebait or any other "fatty fish". Microbial oil or its concentrated form for use in the present invention may be obtained from, for example, algae (including microalgae) or fungi. The microalgae may be, for example, *Crypthecodiniumcohnii* or a *Schizochytrium* sp. The fungi may be, for example, *Mortierellaalpine*. Plant oils or their concentrated form for use in the present invention may be obtained from, for example, rice bran oil, corn oil, soybean oil, canola oil, palm oil, rapeseed oil, sunflower oil, peanut oil, coconut oil, olive oil, safflower oil, linseed oil, grapeseed oil, sesame oil, hazelnut oil, cotton seed oil and the like.

The internal oil phase may be selected depending on the PUFAs which are to be included in the emulsion compositions. For example, if it is desired to include DHA as the LCPUFA, then an oil comprising DHA, such as tuna oil, would be selected as the internal oil phase. The internal oil phase may comprise, consist or consist essentially of, an oil which is rich in the LCPUFA(s) that are to be included in the emulsion compositions. Oils which are sources of one or more LCPUFAs that find particular application in, or as, the internal oil phase include those sold under the trade names DHASCO® and ARASCO® by DSM, Heerlen, Netherlands, and HiDHA® by Nu-Mega Ingredients, Altona North, Victoria. In embodiments of the invention, the internal oil phase comprises, consists or consists essentially of, fish oil. In some embodiments, the fish oil may be a non-winterised or winterised tuna oil.

In other embodiments of the invention, the LCPUFA(s) may be added to the oil to be used as the internal oil phase by simple admixing prior to preparation of the O/W emulsion.

The external oil phase may comprise, consist or consist essentially of, any edible oils, such as a vegetable oil. Examples of suitable edible oils include, but are not limited to: rice bran oil, corn oil, soybean oil, canola oil, palm oil, rapeseed oil, sunflower oil, peanut oil, coconut oil, olive oil, safflower oil, linseed oil, grapeseed oil, sesame oil, hazelnut oil, cotton seed oil and mixtures thereof. Those skilled in the art will appreciate that other edible oils may also be selected as the external oil phase.

The double emulsions may be prepared according to methods known to those skilled in the art, for instance, those described in EP 0970 741 B1 (to Shiseido Co. Ltd). However, one can appreciate that EP 0970 741 relates to cosmetic preparations.

Figure 3:
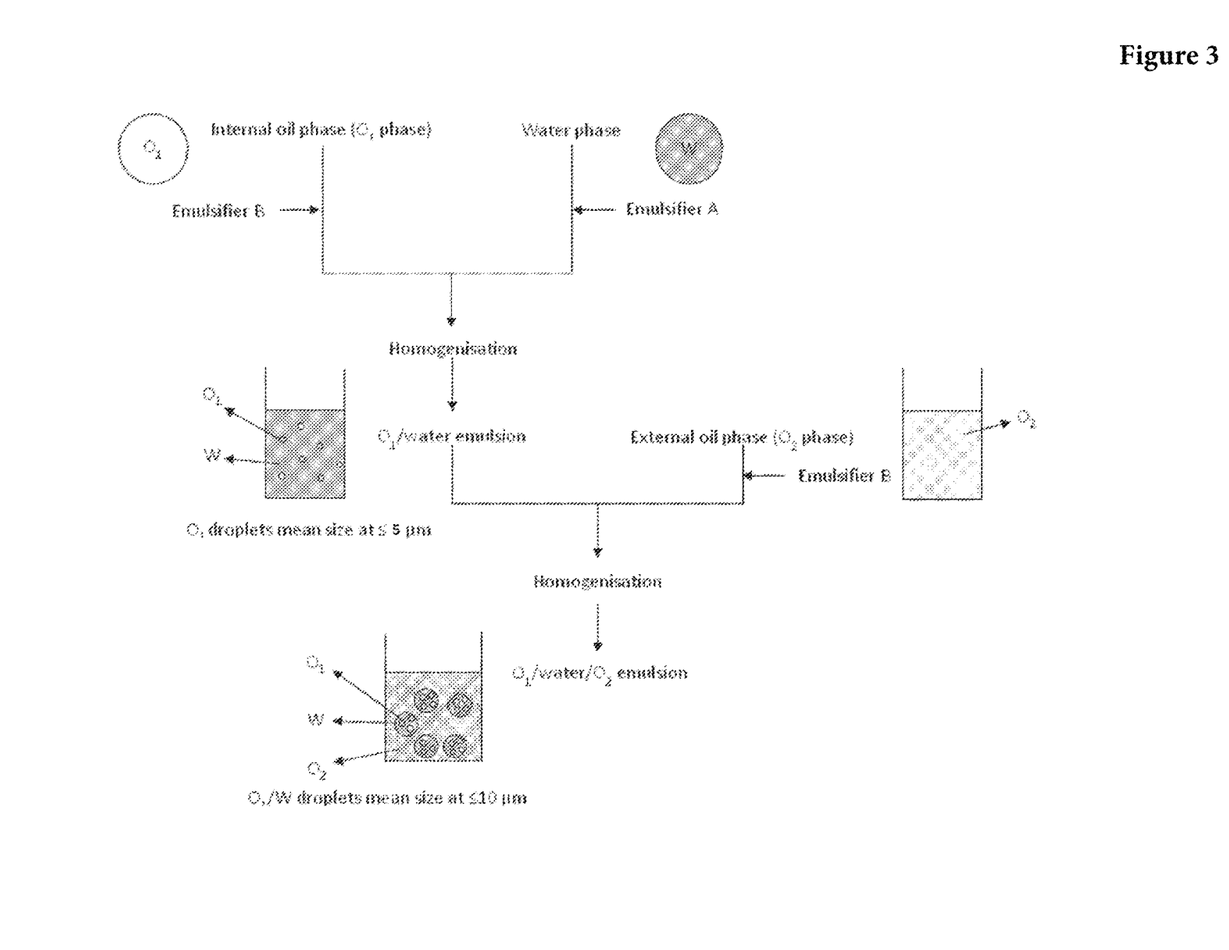
FIG. 3 is a schematic diagram of a process for preparing a nutritional formulation according to the Example 2 embodiment of the invention.

The O/W emulsion may be prepared by combining the oil selected as the internal oil phase (which includes the one or more LCPUFAs), water and emulsifier(s) and mixing until the O/W emulsion is formed. Mixing may be achieved using a high shear mixer. In some embodiments, the emulsifier(s) are added to heated water (for example at a temperature between about 50° C. and 90° C., or at about 55° C., about 60° C., about 65° C. about 70° C., about 75° C., about 80° C., or about 85° C.) and the resultant mixture is subjected to high shear mixing. In an embodiment as depicted in FIG. 3 the oil droplets ($O_1$) in the formed O/W emulsion ($O_1$/W) have a mean size of ≤5 μm such as ≤0.5 μm, ≤0.6 μm, ≤0.7 μm, ≤0.8 μm, ≤0.9 μm, ≤1.0 μm, ≤1.1 μm, ≤1.2 μm, ≤1.3 μm, ≤1.4 μm, ≤1.5 μm, ≤1.6 μm, ≤1.7 μm, ≤1.8 μm, ≤1.9 μm, ≤2.0 μm, ≤2.1 μm, ≤2.2 μm, ≤2.3 μm, ≤2.4 μm, ≤2.5 μm, ≤2.6 μm, ≤2.7 μm, ≤2.8 μm, ≤2.9 μm, ≤3.0 μm, ≤3.1 μm, ≤3.2 μm, ≤3.3 μm, ≤3.4 μm, ≤3.5 μm, ≤3.6 μm, ≤3.7 μm, ≤3.8 μm, ≤3.9 μm, ≤4.0 μm, ≤4.1 μm, ≤4.2 μm, ≤4.3 μm, ≤4.4 μm, ≤4.5 μm, ≤4.6 μm, ≤4.7 μm, ≤4.8 μm, or ≤4.9 μm. Accordingly, an advantage provided by the selected size of the oil droplets ($O_1$) is that the stability of the resultant $O_1$/W emulsion is maintained. A subsequent advantage of the selected size of the oil droplets ($O_1$) is stability of the resultant O/W/O emulsion is provided. Another advantage of the selected size of the oil droplets ($O_1$) is that the $O_1$/W emulsion is formed, which is required to facilitate the preparation of the O/W/O emulsion.

The oil selected as the internal oil phase is then mixed with the water/emulsifier mixture and the resultant mixture subjected to high shear mixing so as to form the O/W emulsion. In other embodiments, the emulsifier(s) are added to heated water (at, for example, a temperature as defined above) and the oil selected as the internal oil phase, and the resultant mixtures are subjected to high shear mixing. The oil/emulsifier and water/emulsifier mixtures are then combined and subjected to high shear mixing so as to form the O/W emulsion.

Formation of the O/W/O emulsion can be accomplished by dispersing the O/W emulsion into the oil selected as the external oil phase and mixing for a sufficient time period. In an embodiment as depicted in FIG. 3 the oil/water droplets in the resultant O/W/O emulsion ($O_1$/water/$O_2$) have a mean size of about ≤10 μm, such as ≤5.0 μm, ≤5.5 μm, ≤6.0 μm, ≤6.5 μm, ≤7.0 μm, ≤7.5 μm, ≤8.0 μm, ≤8.5 μm, ≤9.0 μm, or ≤9.5 μm. Accordingly, in the hands of the present inventors, it has been shown that an advantage has been provided by the selected size of the oil-in-water droplets in the resultant $O_1$/W/$O_2$ emulsion, specifically that encapsulation of the oil-in-water ($O_1$/W) droplets in the emulsion is ensured. Another advantage that may be provided by the selected size of the oil-in-water droplets is that the physicochemical stability of the final $O_1$/W/$O_2$ emulsion is also ensured. In an embodiment, the size of the oil/water droplets in the O/W/O emulsion is selected to ensure encapsulation of the oil-in-water droplets, such that physicochemical stability of the final O/W/O emulsion is not compromised.

The mixing time required may be determined by observing the emulsion periodically using an optical microscope or by monitoring the viscosity of the emulsion. Those skilled in the art are capable of recognising an O/W/O emulsion as an emulsion where the oil-in-water droplets are dispersed in the external oil phase. Mixing may be conducted using a mechanical mixer, such as but not limited to, paddle mixers and concentric ring type mixers, at a speed between about 100 rpm and 10000 rpm, for example about 700 rpm.

In some embodiments, the O/W/O emulsion is formed by phase inversion by mixing equal parts (by mass) of the O/W emulsion and the oil selected as the external oil phase and mixing with a high speed mixer (for example at about 6000 rpm) at elevated temperature (for example about 50° C.). Once a coarse emulsion is formed, stirring is slowed and the emulsion is cooled (for example to a temperature of about −5° C.). The viscosity of the emulsion is monitored for a sharp drop that is indicative of phase transition, for example, a drop of 1000 cps.

Alternatively, the O/W/O emulsion may be formed by mixing equal parts (by mass) of the O/W emulsion and a homogenised mixture comprising the oil selected as the external oil phase and one or more emulsifiers. The components are mixed with a high speed mixer (for example at about 6000 rpm) at elevated temperature (for example about 50° C.). Once a coarse emulsion is formed, stirring is slowed and the emulsion is cooled (for example to a temperature of about −5° C.). The emulsion is monitored for a sharp drop in viscosity which is indicative of phase transition.

In an embodiment, the O/W/O emulsion prepared by phase inversion or by multiple homogenisation may be formed via multiple homogenisation steps. Each homogenisation step may vary in either shear speed, homogenisation pressure or both. The shear speed and/or the homogenisation pressure may be varied for each homogenisation step, the variation of which results in the energy at which homogenisation is performed being varied. In an embodiment, homogenisation can be performed with a high input of energy. In another embodiment, homogenisation can be performed with a low input of energy. In an embodiment, the O/W/O emulsion is formed via multiple homogenisation steps, where the shear speed is varied. In another embodiment, the O/W/O emulsion is formed via multiple homogenisation steps, where the homogenisation pressure is varied.

In another embodiment, the O/W/O emulsion is formed via multiple homogenisation steps, where the shear speed and the homogenisation pressure are varied. In an embodiment, the oil-in-water emulsion is formed by homogenisation of the inner oil phase in the water phase. In another embodiment, the oil-in-water emulsion is formed by homogenisation of the inner oil phase in the water phase in the presence of a high HLB emulsifier. In another embodiment, the oil-in-water emulsion is formed by homogenisation of the inner oil phase with the water phase in the presence of a high HLB value emulsifier with high energy input. In an embodiment, a high energy input means a homogenisation pressure of about 200 to about 600 bar.

In an embodiment, where the O/W/O emulsion may be formed from an oil-in-water emulsion, the oil-in-water emulsion is homogenised at high pressure. In an embodiment, where the O/W/O emulsion may be formed from an oil-in-water emulsion, the oil-in-water emulsion is homogenised to produce oil droplets with a mean size of ≤2 μm. In an embodiment, the oil-in-water emulsion may be produced by sequential homogenisation steps. In an embodiment, the oil-in-water emulsion may be produced by a first homogenisation step, where a water phase comprising a high HLB-value emulsifier and an oil phase comprising a low HLB-value emulsifier may be combined to produce a coarse emulsion. In an embodiment, the oil-in-water emulsion may be produced by a second homogenisation step, where a coarse emulsion produced as a result of a first homogenisation step may be further homogenised. In an embodiment, a second homogenisation step to produce an oil-in-water emulsion may be performed at high pressure. In an embodiment, a second homogenisation step performed at high pressure may produce an oil-in-water emulsion. In an embodiment, a second homogenisation step performed at high pressure may produce an oil-in-water emulsion with a mean oil droplet size of ≤5 μm.

In relation to these embodiments, homogenisation may involve a component comprising a high HLB value emulsifier. In an embodiment, a high HLB value emulsifier has an HLB value greater than 10. In relation to these embodiments, homogenisation may involve a component comprising a low HLB value emulsifier. In an embodiment, a low HLB value emulsifier has an HLB value lower than 10.

In an embodiment, the O/W/O emulsion may be formed via dispersion of the inner oil-in-water emulsion in the external oil phase in the presence of a low HLB value emulsifier. In another embodiment, the O/W/O emulsion may be formed via dispersion of the inner oil-in-water emulsion in the external oil phase in the presence of a low HLB value emulsifier with low energy input. In an embodiment, a low energy input means a shear rate of about 700 rpm.

In an embodiment, the O/W/O emulsion may be formed via homogenisation of an oil-in-water emulsion with an external oil phase. In an embodiment, the O/W/O emulsion may be formed via homogenisation of an oil-in-water emulsion with an external oil phase in the presence of a low HLB-value emulsifier. In an embodiment, the O/W/O emulsion may be formed via homogenisation of an oil-in-water emulsion and an external oil phase at high pressure or high speed. In an embodiment, homogenisation of an oil-in-water emulsion and an external oil phase at high pressure may produce a coarse double emulsion. In an embodiment, the O/W/O emulsion may be formed via homogenisation of a coarse double emulsion. In an embodiment, the O/W/O emulsion may be formed via homogenisation of a coarse double emulsion obtained via the homogenisation of an oil-in-water emulsion and an external oil phase. In an embodiment, the O/W/O emulsion may be formed via homogenisation of a coarse double emulsion. In an embodiment, the O/W/O emulsion may be formed via homogenisation of a coarse double emulsion at high pressure. In an embodiment, homogenisation of a coarse double emulsion at high pressure may produce an O/W/O emulsion with a mean droplet size of ≤10 μm. In an embodiment, homogenisation of a coarse double emulsion at high pressure may produce an O/W/O emulsion with a mean oil-in-water droplet size of ≤10 μm. The oil that is mixed with the double emulsion typically comprises, consists or consists essentially of one or more edible oils. Examples of suitable edible oils include, but are not limited to: rice bran oil, corn oil, soybean oil, canola oil, palm oil, rapeseed oil, sunflower oil, peanut oil, coconut oil, olive oil, safflower oil, linseed oil, grapeseed oil, sesame oil, hazelnut oil, cotton seed oil and mixtures thereof. The oil that is mixed with the double emulsion may further comprise additional components commonly included in infant formula, such as fat-soluble vitamins.

The method may further comprise mixing the LCPUFA-containing oil mixture with an aqueous phase to provide an O/W emulsion, and subsequently spray-drying the O/W emulsion.

Figure 1:
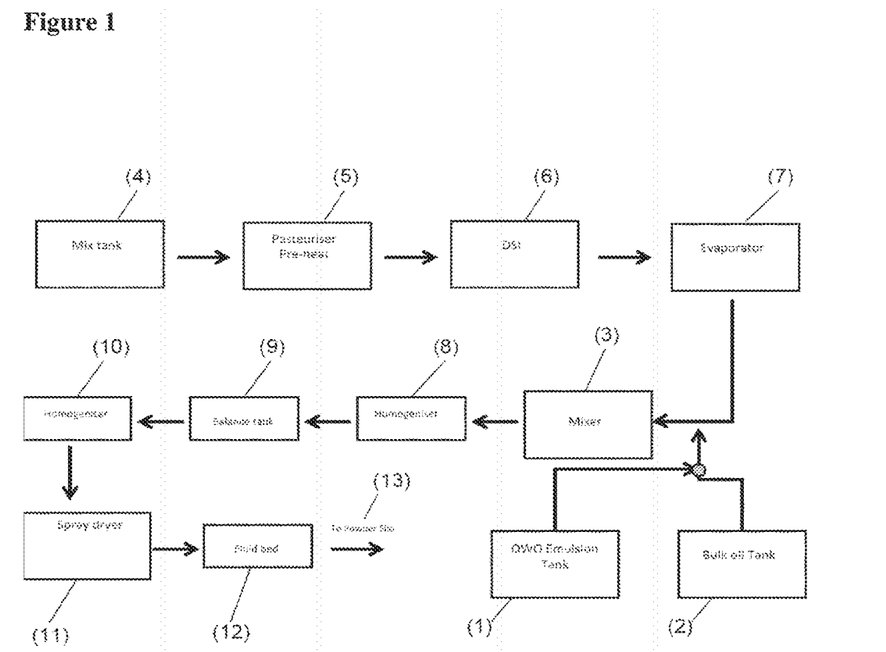
FIG. 1 is a schematic diagram of a process for preparing a nutritional formulation according to an embodiment of the invention.

FIG. 1 illustrates an example of a method according to the present invention. The double emulsion (O/W/O) is prepared in a tank (1), for instance as detailed in Example 1. The tank may be kept at a temperature to maintain phase inversion, and optionally at a temperature of about 50° C. to 80° C. prior to injection into the bulk edible oil phase. The O/W/O emulsion is added to the bulk carrier oil (i.e., edible oil) that is contained in the bulk oil tank (2). The flow rates of the O/W/O emulsion into the carrier oil may be in the range of about 10 kg/hr to 40 kg/hr. The flow rate of the mixed emulsion/bulk carrier oil into the mixing tank (3) may be increased to a rate of about 300 to 700 kg/hr depending on the concentration of O/W/O emulsion to carrier edible oil required in the emulsion. Further ingredients may be added to mixing tank (3) such as vitamins and sugars (which may be used as sweeteners or sources of energy). Also, to mixer (3) may be added ingredients that may require additional processing prior to being mixed with the O/W/O emulsion. This may include other raw materials that may be processed by mixing (4), pasteurisation (5), direct steam injection (6), and evaporation (7) before entering mixer (3). The mixture in (3) may then be processed via a dual homogenisation system including (8), (9) and (10) and then transferred to a spray dryer (11). Other process parameters may include particle separation through fluid bed means (12), and spraying of wetting agents or addition of other ingredients, and storage of the resulting formulation powder (13).

An O/W/O emulsion formed by a method of the invention may be analysed by conventional means known in the art to confirm formation of the double emulsion. Suitable means of analysis, including structural analysis, are known to those of skill in the art, and the analysis may be conducted using no more than routine experimentation. Suitable means of analysis include cryo-SEM (Scanning Electron Microscopy), TEM (Transmission Electron Microscopy) and confocal scanning laser microscopy, such as described in, for example, "*Characterisation of a double emulsion system (oil-in-water-in oil emulsion) with low solid fats: microstructure*" F. Jahaniaval et al. JOACS, Vol. 80, No. 1 2003, pages 25 to 31, the contents of which are hereby incorporated by reference.

Aspects of the present invention provide nutritional formulations when produced by methods of the invention. The nutritional formulation may be, for example, a nutritional supplement or an infant formula or may be used as, or in, a nutritional supplement or an infant formula.

The nutritional formulation may further comprise one or more antioxidants or preservatives. Suitable antioxidants are well known to those skilled in the art and may include, but are not limited to green tea extract, tocopherols, tocotrienols and ascorbic acid, including salts and derivatives thereof. The nutritional formulation may comprise a water-soluble antioxidant and/or a lipid-soluble antioxidant. In one embodiment, the nutritional formulation may comprise an ascorbate salt, such as sodium ascorbate, and a lipid-soluble ascorbate derivative, optionally a fatty acid ester of ascorbic acid, optionally ascorbylpalmitate.

The nutritional formulation of the invention may further comprise one or more anti-caking agents. Anti-caking agents that are compatible with the nutritional formulations of the invention will be well known to those skilled in the art and may comprise calcium phosphates, such as tricalcium phosphate and carbonate, such as calcium and magnesium carbonate and silicon dioxide.

The compositions of the invention may further comprise additional components, for example, flavouring agents, colouring agents, vitamins, minerals, amino acids, chelating agents and the like. When nutritional formulations of the invention comprising, for example DHA and AA, are incorporated in an infant formula, the resultant formula is able to provide beneficial levels of DHA and/or AA whilst meeting (or exceeding) current CODEX standards.

EXAMPLES

The invention will now be described in more detail, by way of illustration only, with respect to the following examples. The examples are intended to serve to illustrate this invention and should in no way be construed as limiting the generality of the disclosure of the description throughout this specification.

Example 1

Preparation of O/W/O Emulsion by Phase Inversion

TABLE 1

| O/W/O formulation. | | |
|---|---|---|
| Formulation | Ingredient | % |
| Oil phase A (external) | Soy oil | 85.25 |
| | Water | 14.40 |
| | Low HLB value Emulsifier B | 0.10 |

TABLE 1-continued

O/W/O formulation.

| Formulation | Ingredient | % |
|---|---|---|
| | High HLB value Emulsifier A | 0.26 |
| Oil phase B (internal) | Total | 100.00 |
| | Tuna oil (DHA source) | 81.00 |
| | Water | 18.20 |
| | Low HLB value Emulsifier B | 0.20 |
| | High HLB value Emulsifier A | 0.60 |
| O/W/O emulsion | Total | 100.00 |
| | Oil phase A | 50.00 |
| | Oil phase B | 50.00 |
| | Total | 100.00 |

Methodology:

Oil Phase A

1. Heat water to 50-60° C., add the high-HLB-value emulsifier A for 5 min until fully dissolve (step 1)
2. Warm up oil to 65° C. before taking it to ensure its integrity. Add the low-HLB-value emulsifier B to oil and blend using high shear mixer to break down emulsifier B. Heat oil to 80° C. and hot melt emulsifier B.
3. Cool to 50° C.
4. Slowly pour oil phase into slurry (step 1) while blending at high shear 15000 rpm for 5 min.
5. Hold temperature constant at 50° C. while preparing the oil phase B.

Oil Phase B

1. Heat water to 50-60° C., add high-HLB-value emulsifier A for 5 min until fully dissolve (step 1).
2. Warm up oil to 65° C. before taking it to ensure its integrity. Add the low-HLB-value emulsifier B to oil and blend using high shear mixer to break down emulsifier B. Heat oil to 80° C. and hot melt emulsifier B.
3. Cool to 50° C.
4. Slowly pour oil phase into slurry (step 1) while blending at high shear 15000 rpm for 5 min.
5. Hold temperature constant at 50° C. while preparing the oil phase A.

O/W/O Emulsion

1. Take equal parts oil phase A and oil phase B held at 45-50° C.
2. Form course emulsion using puddle mixer (600 rpm) mixing for 5 min.
3. Place coarse emulsion in water bath at −5° C. (salt and ice bath) while mixing continuously under low shear rate (puddle mixer, 300 rpm).
4. Monitor emulsion viscosity at base line and 5 min intervals for 1 hr. A sharp drop in viscosity indicating phase transition.

Example 2

Preparation of O/W/O Emulsion by Multiple Homogenisation

TABLE 2

O/W/O formulation.

| Formulation | Ingredient | % |
|---|---|---|
| $O_1$/W phase | Tuna oil (DHA source, $O_1$ phase) | 50.00 |
| | Water | 49.20 |
| | Low HLB value Emulsifier B | 0.20 |
| | High HLB value Emulsifier A | 0.60 |
| | Total | 100.00 |
| $O_1$/W/$O_2$ emulsion | $O_1$/W phase | 30.00 |
| | Soy oil ($O_2$ phase) | 68.50 |
| | Low HLB value Emulsifier B | 1.50 |
| | Total | 100.00 |

Methodology $O_1$/W Emulsion

1. Heat water phase to 50-60° C., add a high-HLB-value emulsifier for 5 min until fully dissolve.
2. Warm up internal oil phase ($O_1$ phase) to 65° C. before taking it to ensure its integrity, add low-HLB-value emulsifier B to oil and heat oil to 80° C. to hot melt emulsifier B.
3. Cool to 50° C.
4. Slowly pour internal oil phase into water phase while blending to prepare a coarse emulsion.
5. Homogenise the coarse emulsion further using high pressure homogeniser for a fine $O_1$/W emulsion, with suspending oil droplet mean size at ≤5 μm.
6. Hold temperature constant at 50° C.

$O_1$/W/$O_2$ Emulsion

1. Warm up external oil phase ($O_2$ phase) to 65° C. before taking it to ensure its integrity, add low-HLB-value emulsifier to oil and heat oil to 80° C. to hot melt emulsifier B.
2. Cooled to 50° C.
3. Add $O_1$/W emulsion dropwise slowly to external oil phase ($O_2$ phase) while blending to prepare a coarse double emulsion.
4. Homogenise the coarse emulsion further using high pressure homogeniser to achieve a fine double emulsion ($O_1$/W/$O_2$ emulsion), with suspending $O_1$/W droplet mean size at ≤10 μm.

TABLE 3

CODEX compliant infant formula formulation containing above O/W/O emulsion to deliver target 70 mg DHA per 100 g of powder Infant formula

| Input per tonne finished formula | kg |
|---|---|
| Water | 1328 |
| Milk, non-fat skim | 163.5 |
| Demineralised sweet whey | 433.5 |
| L-Tryptophan | 0.05 |
| Fat-blend | 261.2 |
| Lactose edible | 26.6 |
| Vitamin premix-fat soluble | 0.2 |
| Vitamin premix-water soluble | 1.0 |
| Mineral premix | 11.1 |
| Taurine, synthetic | 0.431 |

TABLE 3-continued

CODEX compliant infant formula formulation containing above O/W/O emulsion to deliver target 70 mg DHA per 100 g of powder Infant formula

| Input per tonne finished formula | kg |
| --- | --- |
| Levocarnitine | 0.0482 |
| Choline chloride | 0.003645 |
| Inulin, oligofructose | 6.5 |
| Galacto-oligosaccharides | 122.8 |
| Nucleotide blend | 0.285 |

TABLE 4

Target process parameters for production of formulation detailed in Table 2. NB exact parameters are detailed in block diagram.

| Parameter | |
| --- | --- |
| Reconstituted aqueous solids | 20.00% |
| Aqueous slurry solids-post evaporator | 36.40% |
| Oil specific gravity (SG) at 65° C. | 0.9062 |
| Aqueous SG at 65° C. | 1.107 |
| Oil load target | 26.20% |
| Total aqueous flow | 9000 kg/hr |
| Oil mass flow | 625 kg/hr |
| O/W/O emulsion flow to bulk oil stream | 17.5 kg/hour |
| O/W/O emulsion hold temperature | 55-60° C. |
| Total solids feed to dryer | 43% |
| Feed rate to dryer | 5500 kg/hr |
| Powder flow rate | 2500 kg/hr |

TABLE 5

Oil blend (as listed in Table 2 formulation)

| Oil | % |
| --- | --- |
| Canola | 23.23 |
| High oleic sunflower | 9.84 |
| Coconut | 23.66 |
| Palm | 33.44 |
| Sunflower | 8.85 |
| Lecithin | 0.98 |

TABLE 6

Water soluble vitamin pre-mix (assumes 10% overage over Label declaration) - as listed in Table 2 formulation.

| Vitamin | % |
| --- | --- |
| Nicotinamide (mg) | 3.33 |
| Vitamin B1 (mg) | 0.48 |
| Vitamin B2 (mg) | 0.00 |
| Vitamin B6 (mg) | 0.29 |
| Vitamin B12 (mcg) | 0.46 |
| Folic acid (mg) | 0.13 |
| Pantothenic acid (mg) | 1.44 |
| Biotin (mg) | 0.01 |
| Lactose (mg) | 6.13 |
| Ascorbic acid | 30.30 |
| Edible lactose (carrier) | 57.44 |

TABLE 7

Nucleotide premix as listed in Table 2 formulation.

| Nucleotide | % |
| --- | --- |
| Nucleotide, cytidine-5'-monophosphate | 46.24 |
| Nucleotide, uridine-5'-monophosphate, disodium salt | 22.51 |
| Nucleotide, adenosine-5'-monophosphate | 13.47 |
| Nucleotide, inosine-5'-monophosphate, disodium salt | 9.49 |
| Nucleotide, guanosine-5'-monophosphate, disodium salt, heptahydrate | 8.29 |

TABLE 8

Mineral premix as listed in Table 2 formulation.

| Mineral | % |
| --- | --- |
| Calcium carbonate | 39.49 |
| Magnesium chloride (hexahydrate) | 13.70 |
| Sodium citrate (dihydrate) | 11.91 |
| Potassium hydroxide | 6.37 |
| Ferrous sulfate, heptahydrate | 2.58 |
| Potassium citrate, monohydrate | 4.36 |
| Zinc sulfate, heptahydrate | 1.39 |
| Potassium iodide | 1.02 |
| Copper sulphate, pentahydrate | 0.12 |
| Potassium chloride | 18.83 |
| Manganese sulfate, monohydrate | 0.001 |
| Sodium selenite (0.3% Selenium) | 0.16 |
| Tricalcium phosphate | 0.07 |

TABLE 8

Fat soluble vitamin premix as listed in Table 2 formulation

| Input | % |
| --- | --- |
| Mixed carotenoids (30% suspension) | 0.22 |
| Vitamin E (DL-alpha tocopheryl acetate) | 33.69 |
| Coconut oil | 66.09 |

Determination of Oxidative Stability Using Induction Period and Slope

Figure 2:
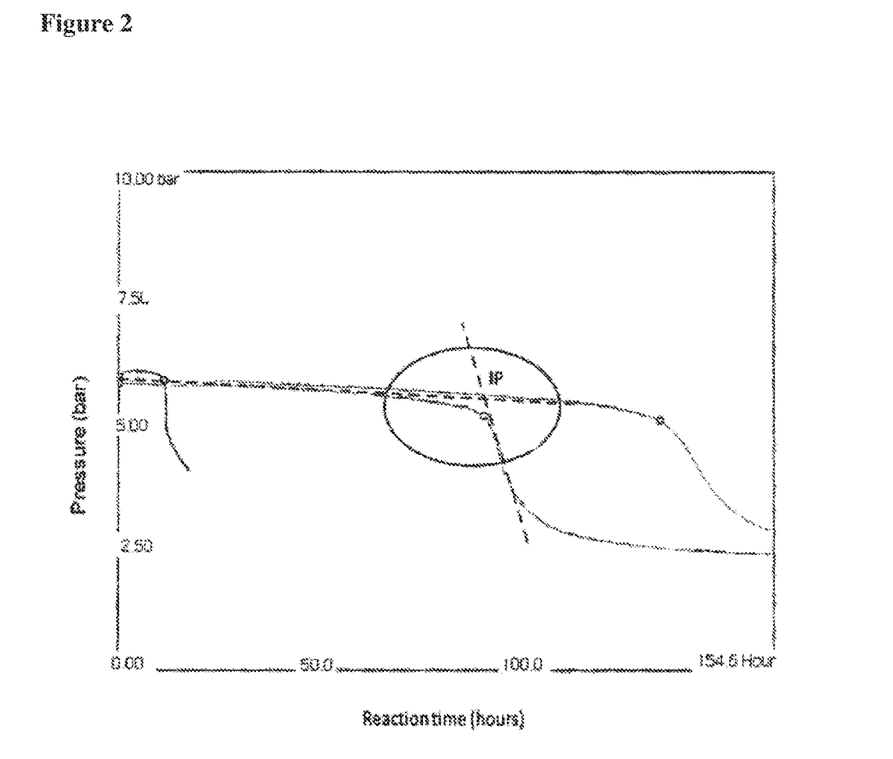
FIG. 2 is a graph of pressure (bar) versus reaction time (hours) of oxygen absorption for the determination of oxidation stability of the formulations of the present invention.

The ML Oxipres is a modification of the Oxygen Bomb method traditionally used for testing efficiency of antioxidants on heterogeneous products containing oils and fats. The ML Oxipres monitors the oxidation of oils and fats in a heterogeneous product and can also be used to monitor oxidative stability of oils and fats. The instrument gives a graph of oxygen absorption over time and the end of the induction period is the point of inflection (see FIG. 2) that is quite clear and sharp. Induction period is the time (in hours) elapsed between placing the pressure vessel in the block heater and the break point at a given temperature/pressure combination. The longer the period of time until "breakpoint" the more stable the oil or heterogeneous product containing the oil (e.g. microencapsulated sample).

The formulation of the present invention may be analysed by ML Oxipres (Mikrolab Aarhus A/S Denmark) to compare the oxidative stability to formulations prepared by other methods.

Emulsion Morphology

Figure 4:
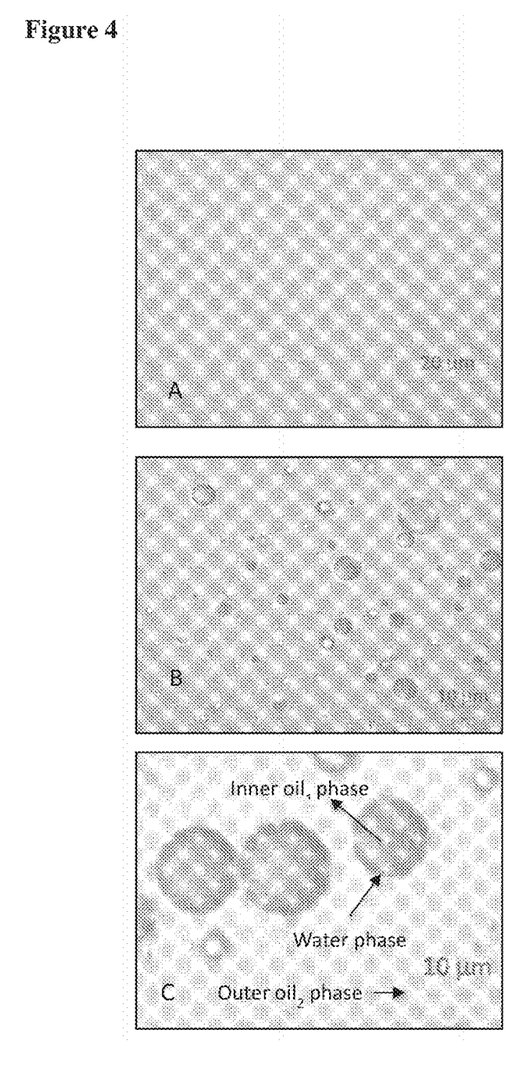
FIG. 4 shows preparation of an O/W/O emulsion according to Example 2. (A) inner oil-in-water emulsion; (B) inner $oil_1$-in-water-in-outer $oil_2$ emulsion and (C) morphology of O/W/O emulsion droplet. Scale bars were as shown.

The morphology of droplets of an O/W/O emulsion prepared in accordance with Example 2 is shown in FIG. 4. During the first homogenisation, inner oil phase ($O_1$) were entrapped in the water phase using emulsifier with higher HLB values so an initial oil$_1$-in-water emulsion was prepared, shown in FIG. 4A. Subsequently, as the dispersed phase, the $O_1$/W emulsion was homogenised again in outer oil continuous phase ($O_2$) in the presence of emulsifier with lower HLB values to produce $O_1/W/O_2$ emulsion, shown in FIG. 4B. The morphology of obtained $O_1/W/O_2$ emulsion droplet can be clearly visualised using a microscope (FIG. 4C).

The invention claimed is:

1. A method for producing a nutritional formulation comprising one or more long chain polyunsaturated fatty acids selected from docosahexaenoic acid (DHA), arachidonic acid (AA), eicosapentaenoic acid (EPA), docosapentaenoic acid (DPA), α-linolenic acid (ALA), stearidonic acid (SDA), linoleic acid (LA), gamma linolenic acid (GLA), conjugated linolenic acid (CLA) or mixtures thereof, said method comprising the steps of:
   (i) providing a double emulsion of said one or more long chain polyunsaturated fatty acids within an edible oil stream:
   (a) preparing a double emulsion (O/W/O emulsion) characterised by an internal oil phase comprising one or more long chain polyunsaturated fatty acids dispersed in an aqueous phase comprising at least one emulsifier which is in turn dispersed in an external oil phase comprising at least one emulsifier and dispersing said double emulsion into an edible oil stream; or
   (b) preparing an oil-in-water emulsion (O/W emulsion) characterised by an internal oil phase comprising one or more long chain polyunsaturated fatty acids dispersed in an aqueous phase comprising at least one emulsifier, and dispersing said O/W emulsion in an edible oil stream comprising at least one emulsifier thereby forming said double emulsion in-situ;
   wherein preparing the O/W emulsion and the O/W/O double emulsion comprises a high-shear mixing step, wherein said high-shear mixing comprises mixing at a speed from about 100 rpm to about 10,000 rpm;
   (ii) mixing the double emulsion of said one or more long chain polyunsaturated fatty acids within the edible oil stream with an aqueous phase; or
   (iii) mixing the double emulsion of said one or more long chain polyunsaturated fatty acids within an aqueous phase; and
   (iv) homogenising the double emulsion mixture of step (ii) or (iii) to form the nutritional formulation,
   wherein the mean size of oil/water droplets in the O/W/O emulsion is ≤10 μm and the mean size of the oil droplets in the O/W emulsion is ≤5 μm.

2. A method according to claim 1 comprising the steps of:
   (i) providing a double emulsion of said one or more long chain polyunsaturated fatty acids within an edible oil stream by preparing a double emulsion (O/W/O emulsion) characterised by an internal oil phase comprising one or more long chain polyunsaturated fatty acids dispersed in an aqueous phase comprising at least one emulsifier, which is in turn dispersed in an external oil phase comprising at least one emulsifier and dispersing said double emulsion into an edible oil stream;
   wherein preparing the O/W/O double emulsion comprises a high-shear mixing step, wherein said high-shear mixing comprises mixing at a speed from about 100 rpm to about 10,000 rpm;
   (ii) mixing the double emulsion of said long chain polyunsaturated one or more fatty acids within the edible oil stream with an aqueous phase; and
   (iii) homogenising the double emulsion mixture of step (ii) to form the nutritional formulation.

3. A method according to claim 1 comprising the steps of:
   (i) providing a double emulsion of said one or more long chain polyunsaturated fatty acids within an edible oil stream by preparing an oil-in-water emulsion (O/W emulsion) characterised by an internal oil phase comprising one or more long chain polyunsaturated fatty acids dispersed in an aqueous phase comprising at least one emulsifier, and dispersing said O/W emulsion in an edible oil stream comprising at least one emulsifier thereby forming said double emulsion in-situ
   wherein preparing the O/W emulsion and the O/W/O double emulsion comprises a high-shear mixing step, wherein said high-shear mixing comprises mixing at a speed from about 100 rpm to about 10,000 rpm;
   (ii) mixing the double emulsion of said one or more long chain polyunsaturated fatty acids within an aqueous phase; and
   (iii) homogenising the double emulsion mixture of step (ii) to form the nutritional formulation.

4. A method according to claim 1, wherein the one or more long chain polyunsaturated fatty acids are selected from DHA, AA, or a mixture thereof.

5. A method according to claim 1, wherein the one or more long chain polyunsaturated fatty acids are present as a component of a microbial oil, a plant oil, a fish oil or their concentrated form.

6. A method according to claim 1, wherein the nutritional formulation is in the form of a nutritional supplement or infant formula.

7. A method according to claim 1, wherein the nutritional formulation is for use in a nutritional supplement or infant formula.

* * * * *